US005323442A

United States Patent [19]
Golovanivsky et al.

[11] Patent Number: 5,323,442
[45] Date of Patent: Jun. 21, 1994

[54] MICROWAVE X-RAY SOURCE AND METHODS OF USE

[75] Inventors: Konstantin S. Golovanivsky, Grenoble, France; Valeri D. Dugar-Zhabon, Moscow, U.S.S.R.

[73] Assignee: Ruxam, Inc., New York, N.Y.

[21] Appl. No.: 843,569

[22] Filed: Feb. 28, 1992

[51] Int. Cl.$^5$ .............................................. H01J 35/00
[52] U.S. Cl. ................................... 378/119; 378/122
[58] Field of Search .............................. 378/119, 122

[56] References Cited

U.S. PATENT DOCUMENTS

| | | | |
|---|---|---|---|
| 4,553,256 | 11/1985 | Moses | 378/119 |
| 4,952,273 | 8/1990 | Popov | 156/643 |

OTHER PUBLICATIONS

Garner et al "An Inexpensive X-ray Source Based On An Electron Cyclotron" *Rev. Sci Instrum.* 61(2), Feb. 1990, pp. 724–727.
Blumenthal "Food Irradiation Toxic to Bacteria, Safe for Humans" *FDA Consumer,* Nov. 1990, pp. 11–15.
Brynjolfsson "Factors Influencing Economic Evaluation Of Irradiation Processing" *Factors Influencing The Economical Application Of Food Irradiation Symposium Proceedings,* 14–18 Jun. 1971, 1973, pp. 13–35.
Popov, "An Electron Cyclotron Plasma Stream Source For Low Pressure Thin Film Production" *Surface and Coatings Technology,* 36 (1988) Apr. pp. 917–925.
Product Literature for ECR System 9200, Plasma Stream Sources Models 904, 904GR, 906, 906GR 908. ECRI on Miller Model 1M601 ECRJr.
Research System, by Microscience, five single pages and one tri-folded document 1990 no month.
Shapoval et al., "Cubic Boron Nitride Films Deposited by Electron Cyclotron Resonance Plasma" *Appl. Phys. Lett.* 57(18), 29 Oct. 1990, pp. 1885–1885.
Popov "Electron Cyclotron Resonance Plasmas Excited By Rectangular and Circular Microwave Modes" *J.V. Sci. Technical A* 8(3) May/Jun. 1990 pp. 2909–2912.
Popov et al., "Microwave Plasma Source For Remote Low Energy Ion Stream" *Rev. Sci. Instrum.,* 61 (1), Jan. 1990 pp. 300–302.
Popov et al., "Electron Cyclotron Resonance Sources For Wide and Narrow Plasma Streams", *Rev. Sci. Instrum.,* 61(1), Jan. 1990 pp. 303–305.
Popov et al., "Electron Cyclotron Resonance Plasma Stream Source For Plasma Enhanced Chemical Vapor Deposition" *J. Vac. Technol.* A7(3) May/Jun. 1989 pp. 914–917.
Balmashnov et al., "Passivation of GaAs by Atomic Hydrogen Flow Produced by the Crossed Beams Method" *Semicond. Sci. Technol,* 5 (1990) pp. 242–245 no month.
Omeljanovsky et al. "Hydrogen Passivation of Defects and Impurities In GaAs and InP" *J. Electronic Materials,* vol. 18, No. 6, 1989 pp. 659–670 no month.

(List continued on next page.)

*Primary Examiner*—Craig E. Church
*Attorney, Agent, or Firm*—Davis Hoxie Faithfull & Hapgood

[57] ABSTRACT

An X-ray source that produces X-rays as a result of igniting an electron cyclotron resonance plasma inside a vacuumated dielectric spherical chamber filled with a heavy atomic weight, non-reactive gas or gas mixture at low pressure. The spherical chamber is located inside a non-vacuumated microwave resonant cavity that is in turn located between two magnets to form a magnetic mirror. Conventional microwave energy fed into the resonant cavity ignites the plasma and creates a hot electron ring which electrons bombard the heavy gas and dielectric material to create an X-ray emission. The X-ray source is suitable for surface and volume sterilization of foodstuffs, packaged goods, medical supplies, blood products and other materials and medical diagnostic and therapeutic devices such as tomography, mammography and radiology.

89 Claims, 5 Drawing Sheets

OTHER PUBLICATIONS

*Food Irradiation,* World Health Organization 1988, pp. 18–43 no month.

Klinger et al., "Feed Radicidation in Israel–An Update", *Food Irradiation Processing Symposium Proceedings,* 4–8 Mar. 1985, pp. 117–126.

Krishnamurthy et al., "Design Considerations For Food Irradiators In Developing Countries" *Food Irradiation Processing Symposium Proceedings,* 4–8 Mar. 1985, pp. 353–363.

Cleland et al. "Electrons Versus Gamma Ray–Alternative Sources For Irradiation Process" *Food Irradiation Processing Symposium Proceedings* 4–8 Mar. 1985, pp. 397–406.

Lagunas-Solar "New Considerations For Radiation Technology Transfer Programmes For Developing Countries", *Food Irradiation Symposium Proceedings* 4–8 Mar. 1985, pp. 499–506.

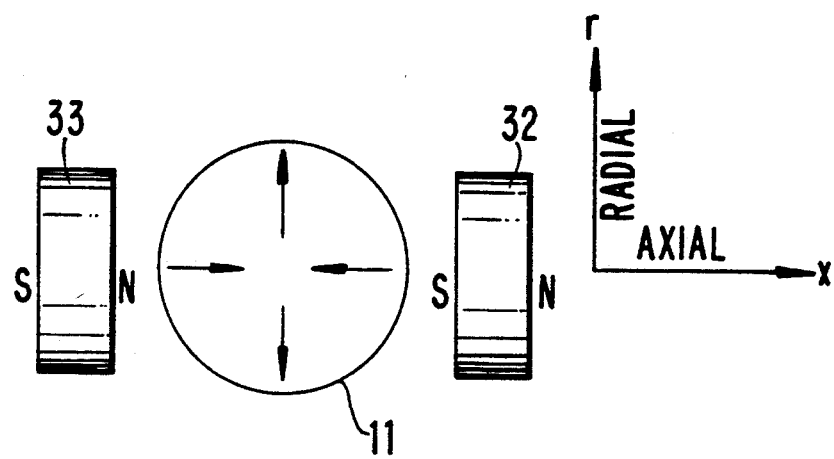
FIG.5
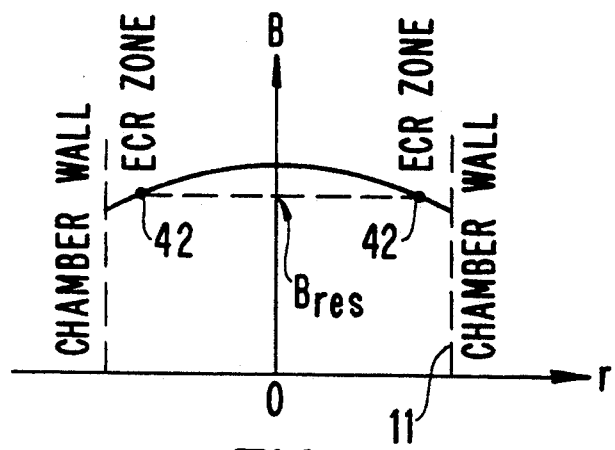
FIG.6
FIG.7
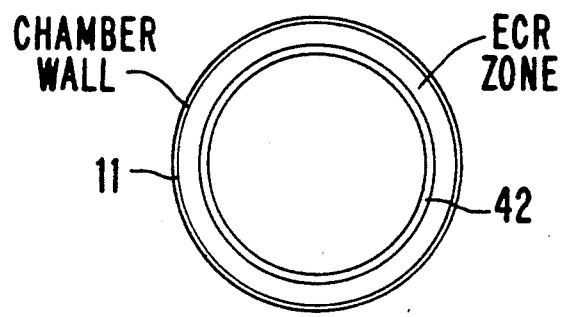

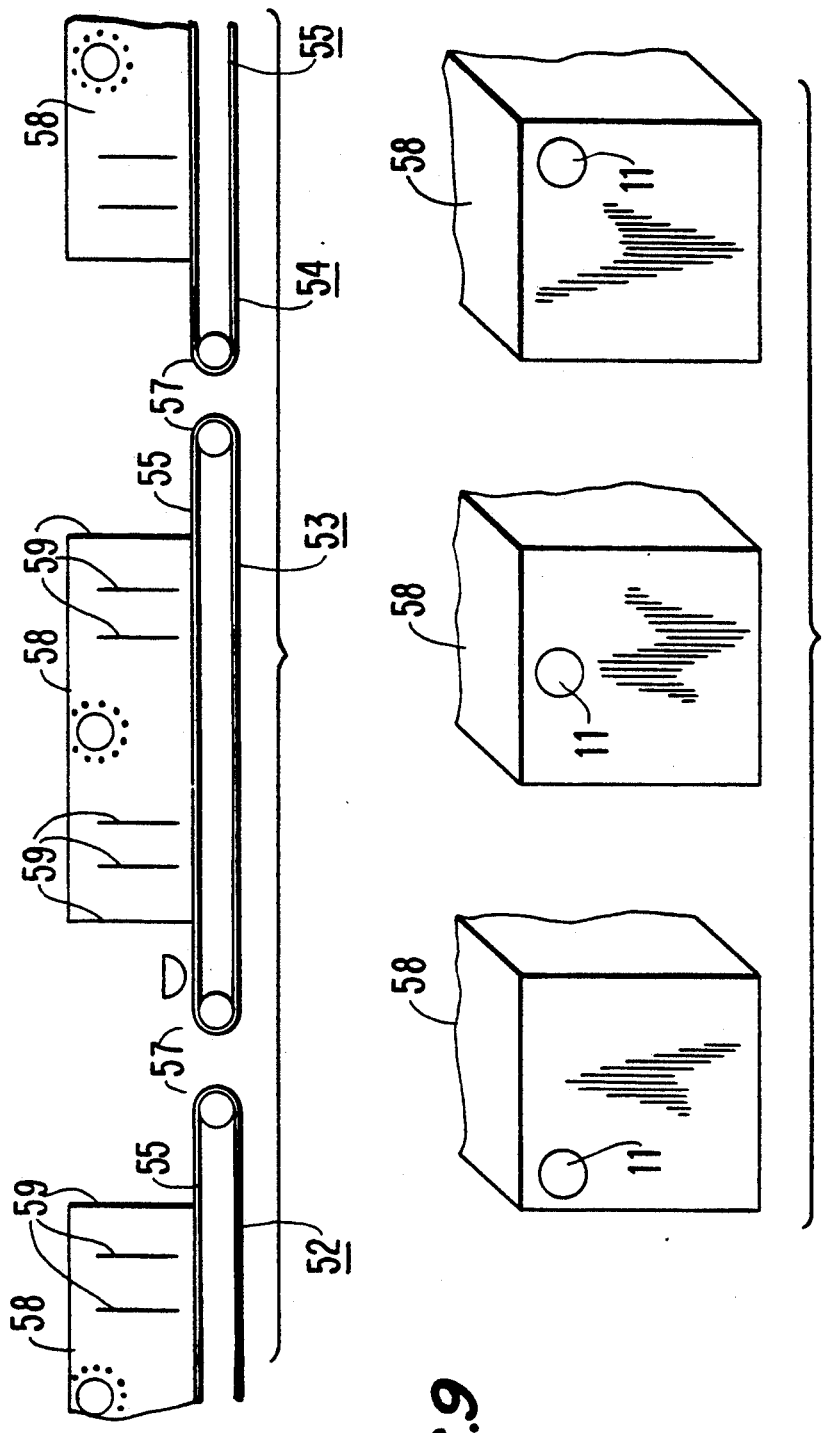
FIG.8
FIG.9
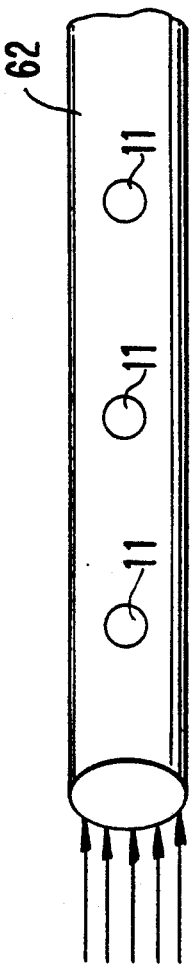
FIG.10

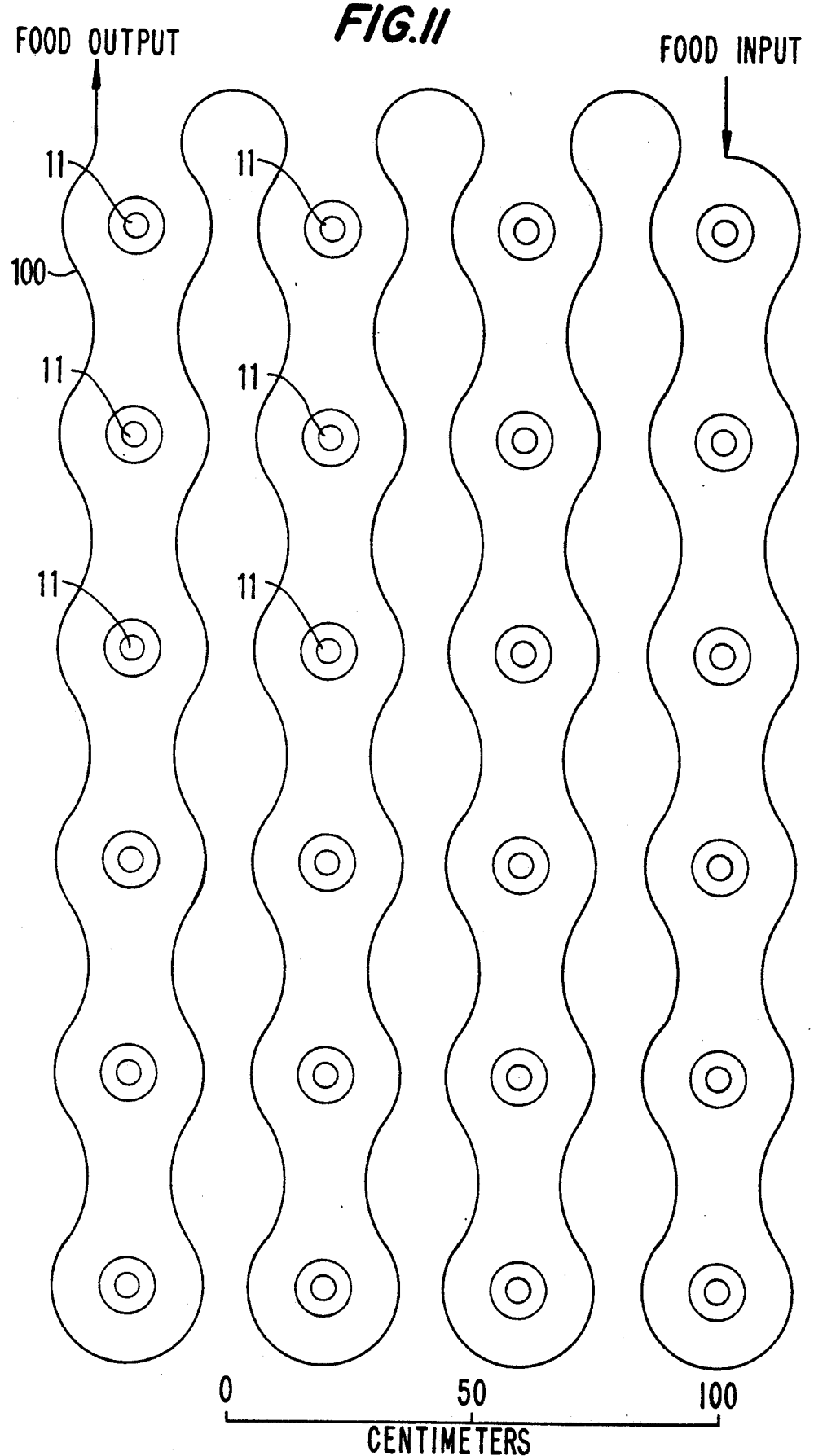

MICROWAVE X-RAY SOURCE AND METHODS OF USE

FIELD OF THE INVENTION

The present invention concerns an X-ray source and method of surface and volume sterilization of such objects as seeds, foods, water, medical supplies and instruments, and numerous other items. More particularly, it concerns the use of an electron cyclotron resonance (ECR) plasma to provide such a source and method.

BACKGROUND OF THE INVENTION

The classical X-ray sources that have been used for sterilization are generally either radioactive nuclides or high voltage vacuum tubes, both of which have limited applications. The radioactive nuclides typically have comparatively short lives and are expensive and dangerous to handle. In addition, the gamma or X-ray intensity they produce cannot be readily monitored and, once activated, the sources cannot be turned off. The high voltage vacuum tube apparatus requires heavy and cumbersome high voltage supplies, which are also dangerous to handle. Further, this apparatus needs highly qualified personnel to operate and maintain it.

To avoid these deficiencies it was recently proposed to use a compact cyclic electron accelerator as a source of X-ray in the range of 150 keV photon energy. See H. R. Gardner, T. Ohkawa, A. M. Howald, A. W. Leonard, L. S. Peranich and J. R. D'Aoust, Rev. Sci. Instruments, 61(2), February 1990, pages 724–727. In this source, the electrons are injected from an electron emitter into a vacuumated resonant cavity, and accelerated by a microwave field along a spiral orbit to a molybdenum target, which produces the X-ray radiation. Although this source advantageously avoids the use of radioactive nuclides and a high voltage supply, it is not a reliable tool for routine use in the industry and agriculture. The reasons are that the emitted X-ray intensity is too weak, and the life of the device is limited by the life of an electron emitter, which cannot readily be replaced without the replacing of the entire vacuumated cavity. Also, since the X-rays are produced by an electron beam striking a molybdenum target, only half of the produced X-rays are reflected from the target, to be useful, while the other half are absorbed in the target and lost. Further, this source cannot produce homogeneous X-ray radiation in all radial directions from a central source, such as is useful, for example, in sterilizing fluids, e.g., water, from a source centrally located within the flow of the fluid as described below.

There remains a continuing need for better sources of X-rays, and in particular for economical X-ray sources having sufficient intensity for surface and volume sterilization of goods and food stuffs.

SUMMARY OF THE INVENTION

The present invention concerns an X-ray source which is free of the above deficiencies and provides nearly the same X-ray intensity and energy as the classical high voltage X-ray sources, although it has a drastically smaller volume, weight, electrical consumption and cost. In addition, the X-ray source of the present invention has no elements, such as microwave coupling elements, electron emitters, targets or the like, within a vacuumated volume. This dramatically increases the stability, reliability, intensity and life of the source. In addition, it does not rely on radioactive nuclides or a high voltage supply, and it is extremely reliable and simple both in operation and maintenance. Advantageously, because of its small size and low cost, the X-ray source of the present invention can be used in small scale operations such as local food processing plants and the like, unlike the known commercial devices which are limited to large sterilization plants. The present invention also concerns using multiple X-ray sources, cascaded in succession along an existing processing or packaging line or assembled in modular units to achieve whatever cumulative amount of X-ray radiation may be desired for a given throughput rate. Moreover, the X-ray sources can be made mobile and easily transported to any location for use.

Broadly, the invention is directed to apparatus and methods for producing X-ray radiation by providing a vacuumated chamber that is made of a dielectric material and is filled with a heavy atomic weight gas at low pressure and placing the chamber in a resonant magnetic field that generates an Electron Cyclotron Resonance (ECR) plasma inside the chamber. The hot electrons of the ECR plasma bombard the heavy gas in the chamber and the dielectric material of the chamber which in turn produces X-ray radiation. The vacuumated chamber is preferably a spherical quartz glass chamber and the heavy gas is preferably xenon gas.

In one embodiment, the ECR plasma is generated by placing the chamber inside a non-vacuumated microwave resonant cavity which is in its turn disposed in a magnetic field, preferably between opposite poles of two permanent magnets. This configuration, when microwave energy is coupled into the resonant cavity, provides a compact axisummetric magnetic mirror configuration with an ECR plasma inside of the chamber with respect of the selected microwave frequency. This is described in greater detail below. The resultant X-ray is emitted homogeneously in the equatorial plane of the cavity perpendicular to the magnetic field axis.

The lateral wall of the resonant cavity is made of a material which is transparent for the X-ray, but is not transparent for the microwave. For example, a light metal, e.g., aluminum, grid having an appropriate mesh size for trapping microwaves is preferred. The electrical (microwave) supply required for this X-ray source (which is referred below as ECR-X) is similar to those of conventional domestic microwave ovens, but it consumes only half of the electrical power ($\sim 1$ kW).

Another aspect of the invention concerns a method of forming a source for use in producing X-rays, which source is a replaceable item of an apparatus for producing X-rays. One method of forming such a source includes the steps of:

forming a chamber of a dielectric material;

evacuating the chamber under conditions of temperature and pressure sufficient to out gas impurities from the dielectric material;

filling the chamber with a heavy atomic weight gas or gas mixture; and sealing the chamber with the pressure inside the chamber being between $10^{-4}$ and $10^{-5}$ Torr.

Another aspect of the present invention concerns apparatus for irradiating a material, article, or product that is being processed or conveyed with X-ray radiation. One such apparatus includes:

a plurality of X-ray sources, each X-ray source comprising:

a microwave resonant cavity;

a sealed vacuumated chamber filled with a heavy atomic weight gas or gas mixture located inside the cavity; and means for applying a magnetic field to the sealed chamber for use in producing an electron cyclotron resonance plasma within the chamber; and means for advancing the material to be exposed to X-rays emitted by one or more of the plurality of X-ray sources.

A cladding, surrounding the advancing means and plurality of X-ray sources, is preferably provided for containing X-rays. The cladding is provided with one or more openings for the entry and exit of materials.

Preferably, the apparatus includes a source of microwave energy, which may be one supply or more than one supply, and a waveguide network for feeding microwaves from the source to the resonant cavity of each of the X-ray sources. The waveguide network may be configured so that each microwave energy source feeds microwaves to more than one X-ray source.

The apparatus further may be built on a movable platform, such as a truck, a trailer attachable to a vehicle, an airplane or other movable structure. The term "truck bed" refers to a platform on a truck or other automotive vehicle or a trailer attachable to another automotive vehicle.

Another aspect of the invention concerns a method for sterilizing water or other flowing material comprising:

(a) forming a flow passageway for passing the water or other material through a defined area;

(b) providing a non radioactive source for producing X-rays inside the flow passageway;

(c) generating X-rays inside the flow passageway at a first intensity;

(d) passing the material in a flow at a first rate through the flow passageway and the X-rays to sterilize the water or other material.

Preferably, the passageway is clad with a material for containing X-rays. They may be more than one non radioactive X-ray source, each source being interposed in the flowpath and spaced apart along the passageway and generating X-rays at an intensity so that the flowing material is cumulatively exposed to an intensity that corresponds to the first intensity. Preferably, each source is an ECR-X source immersed in the flow. Also, the flow passageway may be bent on opposite sides of the X-ray source(s) and cladding applied to the flow passageway between and about the bends so that X-rays generated by the source(s) inside the flow passageway are confined within the flow passageway.

BRIEF DESCRIPTION OF THE FIGURES

Further features of the invention, its nature and various advantages will be more apparent from the drawings and the following detailed description of the invention, in which like reference numerals refer to like elements, and in which:

FIGS. 4a–4c and 5 through 7 show magnetic field lines, field strength and other parameters that are useful in understanding the apparatus shown in FIGS. 1 to 3; and FIGS. 8 through 11 show some of the methods in which the X-ray source of FIGS. 1 to 3 can be employed, FIG. 11 being drawn to the illustrated scale.

DETAILED DESCRIPTION OF THE INVENTION

Figure 1:
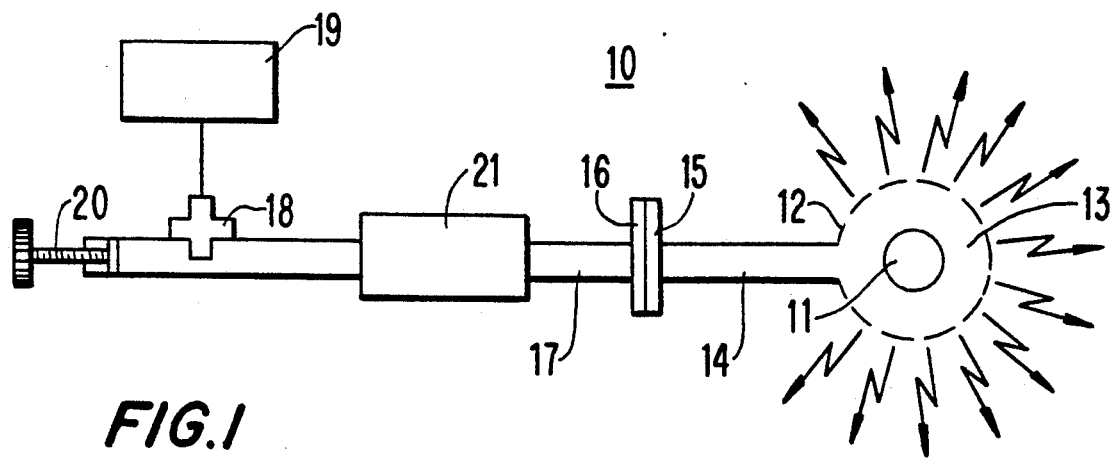
FIG. 1 shows a schematic view of the overall ECR-X source of the present invention.
Figure 2:
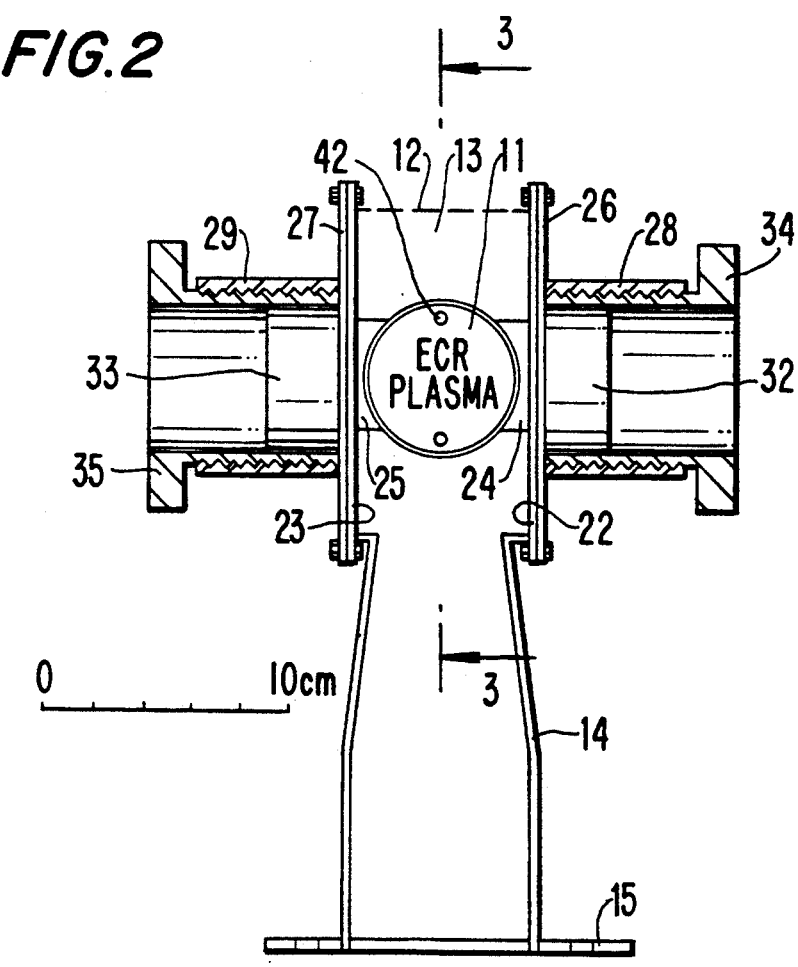
FIG. 2 shows the detailed construction of the radiating block used in FIG. 1, drawn to the scale illustrated in FIG. 2.
Figure 3:
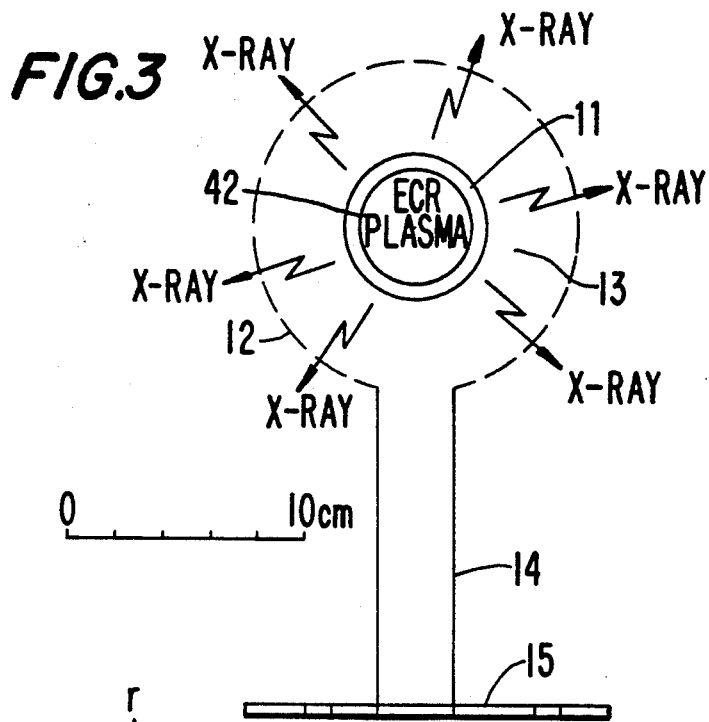
FIG. 3 shows a schematic view of the radiating sphere inside a resonant cavity, drawn to the illustrated scale, as it appears in a section taken along a center-line through FIG. 2.

Referring to FIGS. 1 to 3, there are four basic components in the preferred embodiment of the ECR-X source 10 of the present invention, namely, a spherical chamber 11 filled by a heavy gas at a low pressure, a cylindrical grid 12 that surrounds the chamber 11 and forms a resonant microwave cavity 13, a microwave power source 18, and a magnetic mirror formed by magnets 32 and 33, which is effective within sphere 11, as will be explained. The microwave source and magnets combine to form an electron cyclotron resonance (ECR) plasma within the sphere 11, as will also be explained.

The actual source of the X-ray radiation is the small dielectric sphere 11 filled with a heavy non-reactive gas. The sphere 11 is about the size of a tennis ball, as indicated by the scale shown in FIGS. 2 and 3. This dielectric sphere is preferably made of quartz, but it may be glass or ceramic or other material that will not react with the heavy gas. The gas is preferably xenon, but it also can be krypton or argon, or any other inert gas. Further, the gas can be a heavy non-inert gas, so long as the gas is non-active in relation to the surrounding sphere, or a mixture of gases.

A heavy gas is desired so that it will line the inside surface of chamber 11, absorb a substantial portion of the electrons from a hot electron ring, to be discussed, and emit X-ray energy. Further, the penetration of the atoms of the heavy gas into the dielectric wall of sphere 11 is negligible so that the gas pressure in chamber 11 remains constant during practically unlimited time. In addition, the start-up of a plasma is very easy in heavy gases as compared to light gases due to the smaller mobility of the heavy ions. Also the electron density reached in the heavy gas plasma is higher than in light gases at the same microwave power, because of the reduced losses due to the low mobility of the heavy ions.

The sphere 11 is filled with the heavy gas in a well-known manner, for example, by evacuating the sphere on a commercially available vacuum pump, at an elevated temperature, to out gas any impurities in the quartz or other material of the sphere, in order to ensure prolonged life of the sphere as an X-ray source. Once evacuated and processed to remove impurities, the sphere is filled with the heavy gas, and the tubulation used for out-gassing and filling is sealed.

In the preferred embodiment, the X-ray source apparatus includes a non-vacuumated cylindrical resonant cavity 13 which resonates in the $TE_{111}$ mode. Cavities that resonate in other modes that have the electrical field component perpendicular to the static magnetic field axis also may be used. Cavity 13 is preferably formed of a grid 12, preferably made of beryllium or aluminum. The cavity 13 is about 1 liter in volume and it encompasses the closed spherical dielectric chamber 11.

Microwave power is passed into cavity 13 through the waveguide 14, which is connected through the flanges 15 and 16 with the waveguide 17 that supplies microwave energy from an oscillator 18, which may be a magnetron fed from an electrical supply 19. The microwave energy from oscillator 18 is preferably at a frequency of 2.45 GHz. The coupling between the magnetron 18 and the waveguide is conventionally optimized by means of a movable plunger 20 which may be mounted on a slide or threads for adjusting its position. The magnetron is protected against any reflected microwave energy by a conventional circulator device 21.

FIGS. 2 and 3 show the construction of the X-ray radiating block in some detail. As shown in these figures, the resonant cavity is composed of a cylindrical lateral wall 12 and two flanges 22 and 23. The cylindrical wall 12 is made of a grid of light metal, such as beryllium or aluminum. The grid 12 contains the microwave energy employed, at 2.45 GHz, but is transparent to the X-rays emitted from sphere 11. If necessary, the base material of the grid 12, such as beryllium or aluminum, is preferably coated with a thin coating of high electrical conductivity material, such as copper, to minimize its heating. The coating can be about 10 micrometers thick. Moreover, air cooling (ambient or forced) of the grid 12 and resonant cavity 13 is advantageously employed to provide the quartz chamber cooling.

Grid 12 is attached to a rectangular waveguide section 14 which is connected with the microwave supply 18 through the flange 15. The cylindrical wall 12 is fixed between the two flanges 22 and 23, which can be made of duraluminum or copper, and two dielectric cushions 24 and 25 which serve to support the spherical plasma chamber 11 within the resonant cavity. These dielectric cushions are preferably porous teflon, and they may be mechanically attached to flanges 22 and 23. Alternatively, the cushions may be a foam material or any other cushioning dielectric non-magnetic material that can be appropriately shaped and secured to support sphere 11 in place without absorbing microwave energy.

The cylindrical wall 12 and two flanges 22 and 23, once being assembled in the apparatus of FIGS. 1 to 3, form a resonant cavity for the microwave energy at 2.45 GHz. This cavity is fed microwave energy from source 18 through the circulator 21, and waveguide sections 17 and 14, waveguide 14 being tightly connected to the flanges 22 and 23 to minimize any losses. Wave guides 14 and 17 are standard units of copper or aluminum.

As shown in FIG. 2, flanges 26 and 27 are attached by bolts to flanges 22 and 23. A braided copper seal can be inserted between flanges 22 and 26, and between flanges 23 and 27, to be compressed when the bolts attaching the flanges are drawn together, to avoid any microwave energy leakage. Flanges 26 and 27 include cylindrical tubes 28 and 29, which are internally threaded. As shown in FIG. 2, the apparatus also includes two disk-shaped permanent magnets 32 and 33, which are preferably $SmCo_5$, fixed in casings 34 and 35. These casings and tubes 28 and 29 have a common thread, so that the casings can be screw threaded with the tubes, and thereby adjust the position of magnets 32 and 33 by rotating the casings.

The only element of the apparatus that must be occasionally replaced is the sphere 11, which has a nominal useful life of about 1000 hours of operation as the plasma chamber. The cost of this sphere can be quite low, and the replacement operation does not require any special skill. In this regard, the sphere 11 is removably mounted in the cavity 13. To replace the spherical chamber 11, one need only separate one of the flanges 26 or 27, replace the old chamber 11 by a new one, preferably leaving dielectric cushions 24 and 25 in place (unless their replacement is appropriate), and then reattach the flange. This operation can be done in a short time.

To start the ECR-X source, one starts the microwave oscillator 18. This transmits microwave energy at a frequency of 2.45 GHz through the waveguide to the resonant chamber cavity 13. Since the magnets 32 and 33 are in place, the presence of the microwave energy in the chamber 11 causes the ECR plasma to form and the X-ray emission to begin. The X-ray emission is a bremsstrahlung with the peak energy between 100 and 200 keV depending on the microwave power applied, e.g., from 200 to 500 watts. To stop the X-ray emission, one simply turns off the microwave oscillator. This is adequate for many sterilization or preservation methods as disclosed herein.

The effectiveness of any X-ray source to sterilize and preserve food and other materials is a function of the amount of X-ray energy and the time of exposure. According to the present invention, a method of sterilizing an article, a product or materials, in a rapidly moving processing line or the like can be achieved by placing the X-ray sources shown in FIGS. 1 to 3 one after another along the line so that each article or product and all the material advancing along the line receives a cumulative X-ray dose sufficient to cause sterilization. Also, the ECR chambers of successive sources can be offset from one another, so as to irradiate the article or product from different angles.

The food products and other items to be sterilized or preserved using the foregoing X-ray source can be unwrapped or wrapped. It can, for example, include products wrapped in plastic foil, wine in bottles, sterile gauze in a carton, and other covered items, provided that the wrapping is transparent to the X-ray.

An understanding of the operation of the ECR plasma in the sphere 11, and additional insight into the mode of operation of the X-ray source, can be gleaned with reference to FIGS. 4 to 7 and the following discussion.

Figure 4A:
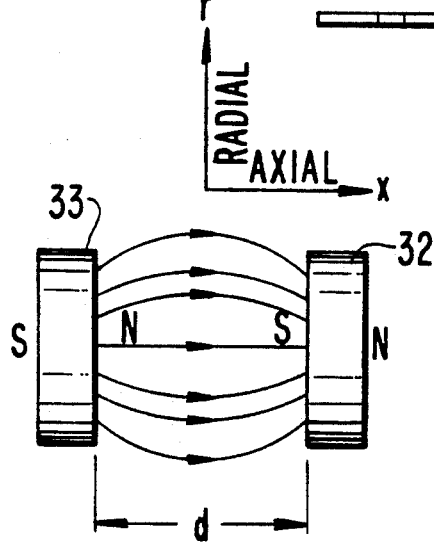
Figure 4B:
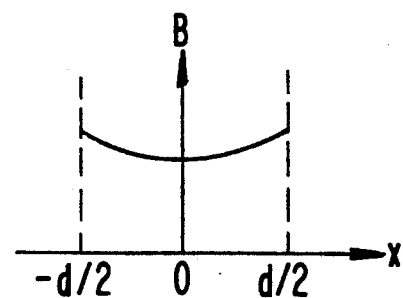

The disk-shaped magnets 32 and 33 in FIG. 2, are shown in FIG. 4(a) with an illustration of the magnetic field lines they produce. Also, the axial and radial directions are depicted. As shown by the closeness of the field lines, the magnetic field increases as one moves from the center of the magnetic field toward either of the magnets, as shown by the graph in FIG. 4(b). Also, it decreases as one moves from the center of the field in a radial direction, as shown by the graph in FIG. 4(c).

In FIG. 5, the arrows within the plasma chamber 11 show the direction of the forces on the plasma particles, which are produced by the magnetic field, to create a well-known magnetic mirror.

Figure 4C:
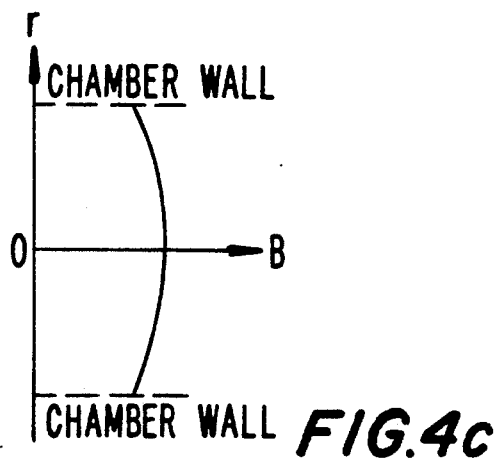

For microwave energy at 2.45 GHz, electron cyclotron resonance (ECR) occurs for a magnetic field strength of 865 gauss. The magnets 32 and 33, and their spacing, are chosen, and adjusted in position, so that the magnetic field strength along the axis between the magnets, as shown in FIG. 4(a), is higher than 865 gauss. This also is true for the field strength at the center of the magnetic field moving in a radial direction. However, as shown in FIG. 4(c), as one nears the spherical chamber wall the magnetic field decreases.

Thus, near the internal surface of the sphere 11, along the centerline between magnets 32 and 33, a point will be reached where ECR resonance occurs, as shown in FIG. 6. This produces an equatorial ring 42 of hot electrons, which has been observed as an associated effect in some past ECR work. See W. D. Dougar-Jabon, K. S. Golovanivsky and V. D. Schepilov, "Accumulation of Multicharged Ions in Plasma with Electrostatic Well Induced by ECR", *Physica Scripta (Sweden)*, Vol. 18, 506–507, 1978.

The hot electron ring 42 also is shown in FIGS. 2, 3 and 7. In the operation of sphere 11, electrons in the hot electron ring spiral off from the ring due to the so-called flute instability, which is a well known physical phenomenon. These spiraling electrons collide with a dense layer of atoms of the gas within sphere 11, and with the internal surface of the sphere. As a consequence, X-rays are emitted in a divergent array, from the heavy gas particles and the material of the sphere 11, along an equatorial region about sphere 11, as shown in FIGS. 1 and 2.

With the magnets 32 and 33 properly positioned, the hot electron ring or an ECR zone 42 will be circular and symmetrical within the sphere 11, and the X-ray emission will consequently be homogeneous along the equatorial region. By a proper adjustment of the magnets, the ECR zone can be properly placed, in proximity to the sphere wall, to achieve the optimum X-ray emission.

Any X-rays passing back through waveguide 14 will diminish in strength and distance, and the divergent nature of the X-rays will cause them to be absorbed by the copper waveguide 14. Also, the waveguide 17 can include a turn to ensure that no X-rays will reach the region of oscillator 18. Alternatively, a waveguide turn can occur just outside one of the cylinders 28 and 29, without disrupting grid 12, so that grid 12 can extend the entire 360° around the ECR plasma in sphere 11. In this fashion, the X-ray radiation can be emitted radially over 360°.

While chamber 11 has been described as a sphere, it can also be ellipsoid in shape. Other shapes, such as a cube, can also be used for chamber 11, so long as the chamber has enough physical strength to withstand the external pressure, but a sphere is preferable both because of its strength and symmetrical shape.

Some of the parameters that are believed to be particularly advantageous are that the microwave resonant cavity 13 has a volume of about 1 liter, height of about 7 cm. and a diameter of 13 cm. The microwave energy is desirably at 300 to 500 watts at the stated frequency of 2.45 GHz. The ECR chamber 11 has a volume preferably about 100 cm$^3$, and it is about 6 cm. in diameter, made of quartz glass, with a wall thickness of 1.0 to 1.5 mm. Also, the gas within the ECR chamber 11 is preferably xenon, at an internal pressure of $10^{-5}$ to $10^{-4}$ Torr. The X-ray peak energy is about 180 keV, with an integral intensity of around 1 watt. Further, the grid 12 is preferably duraluminum, with a thin coating of copper that is about 10 micrometers thick. The dielectric cushions 24 and 25 are preferably porous teflon, and the magnets 32 and 33 are SmCo$_5$ disks, each having a height of about 2.5 cm., a diameter of about 5.5 cm., and a magnetic induction on the surface of about 0.4 Tesla. The magnetic field in the region of the hot electron ring is 865 gauss. The hot electron energy in the ECR plasma in sphere 11 is generally 150 to 250 keV, and the hot electron density is $2 \times 10^9$ per cm$^3$. The ring plasma volume is 3 cm$^3$; the plasma lifetime is 5 microseconds; the hot electron current is about 0.2 milliamps; and the energy delivered to the wall by the hot electrons is about 40 watts.

The source weighs about 20 kgs. and absorbs about 1 kW of electrical power.

If X-ray emission is desired in only a window along the equatorial line of emission, a cylinder of lead can be employed, surrounding the grid 12, to cover the height over which the X-ray emission extends, leaving an opening over the area of the desired window of emission. The window may have a desired shape, e.g., a point source hole, a slit, a rectangle, an annular configuration, etc. Lead having a thickness of 5 mm will suffice. One set of operable dimensions for the grid 12 is to have solid members that are about 1 mm in width or diameter separated by spaces that are about 5 mm.

FIGS. 8 to 11 illustrate various methods of radiating an article (or a product), a stream of articles, or a flow of a material with X-rays, for example, for sterilization or preservation. FIG. 8 shows a series of conveyors, each of which includes a belt 55 and a pair of rollers 57. Tunnels 58 are supported such that the conveyor belt 55 passes through or just below the tunnel, each tunnel having a series of lead or lead rubber curtains 59 of at least 3 mm, more preferably at least 5 mm, thickness. Also, an ECR plasma sphere 11, and the associated elements in FIGS. 1 to 3, are contained in each of the tunnels. An article or material to be sterilized or preserved will pass along the successive conveyors. As it meets a tunnel a first curtain will be pushed aside by the article, or automatically withdrawn as the article is sensed, by a photodetector or microswitch or the like. Successive curtains are preferably spaced so that the first curtain will close before the second curtain is opened. Once the article passes the last input curtain 59, it will be radiated as it continues along the conveyor, and then pass through the successive output curtains. By opening and closing the curtains in succession, no X-ray radiation will escape out of the ends of the tunnel.

Alternatively, a single tunnel can include a series of ECR X-ray plasma sources and, as shown in FIG. 9, successive ones of the sources can be offset in order to radiate different portions of the article By passing articles to be sterilized along the conveyors in FIG. 8, through one or more of the tunnels in FIGS. 8 and 9, the bacteria on the articles can be killed and the articles thereby sterilized. This method of irradiating an article with X-rays can be used for such articles as fruit or vegetables, chicken that may contain salmonella, shell fish or other foods, even wine in bottles, or wrapped meats. Also, it can be used for seeds that are to be used in foods, such as caraway seeds, and seeds that are to be planted. Further, it can be used for medical instruments and supplies, whether loose or packaged.

The present invention also concerns a method for irradiating articles or materials such as whole blood and cellular blood components, for example, to inactivate lymphocytes and some viruses at dosages that are not harmful to the viability of other desired blood cell components. And it can be used for irradiating waste products which may contain blood, viruses, bacteria or other organisms that present a risk of spreading disease or infection if disposed without treatment, such as food processing by-products (e.g., raw chicken scraps), used or disposable medical devices, instruments, supplies and blood contaminated materials, and medical diagnostic test by-products (e.g., blood samples, fluids and cultures).

The method of radiating fruits and other foods with X-rays according to the present invention eliminates the bacteria that causes the food to rot which acts to preserve the foods. Thus, the food can safely be shipped long distances, even over slow (and less expensive) travel routes. Further, fruits and other food can be allowed to ripen on the vines or in the orchards, so as to obtain a mature taste and appearance, as well as food value, and then sterilized locally, using the X-ray source and methods of the present invention, before being shipped to distant markets.

Moreover, since the X-ray source and methods of the present invention can operate on loose or packaged products, the X-ray source can be located in a processing or packaging plant either upstream or downstream of the processing or packaging stations.

The sterilization caused by radiation at doses established by the U.S. Food and Drug Administration may not remove all bacteria, and therefore foods may still require refrigeration, but it materially reduces the level of bacteria present and will prolong shelf life. For treatment of products where human or animal consumption of irradiated products is not a concern, the sterilization dosage may be sufficiently high to kill all undesired bacteria, viruses or other organisms.

FIG. 10 shows a water supply pipe 62, which contains a series of centrally located ECR plasma sources 11, each with its associated elements shown in FIGS. 1 to 3. By passing the water along pipe 62, past the successive ECR plasma channels 11, the bacteria in a water supply can be killed and the water supply thereby sterilized. A similar process could be used for any fluid material flow, whether a gas, liquid or solid (solid, gel or particulate matter) flow.

It is noted that the method of sterilizing water using the non radioactive X-ray source immersed in the flow according to the present invention does not present the potential hazard of contaminating the entire water supply, which hazard would exist if a radioactive X-ray source were to be used for such purposes.

FIG. 11 shows a representation of a small scale sterilization station which includes a total of 24 ECR-X sources 11 arranged in a 4×6 matrix and a conveyor 100 for advancing articles along a path by and between the ECR-X sources. In this embodiment, each pair of a block of six ECR-X sources are coupled by a conventional microwave waveguide to a single microwave magnetron power supply, for example, a 12 kw c.w. commercial supply (not shown). Thus, only two such magnetrons are needed. The conveyor 100 is shown as having a tortuous path which is selected to maximize the dose of X-ray radiated from all directions on the articles being treated. Other paths, as well as more or less ECR-X sources, could be used. The walls surrounding the track, and top and bottom of the station may be sealed to trap the X-rays by an appropriate material, e.g., lead lined walls and the aforementioned curtains for passing articles into and out of the station.

One suitable conveyor 100 is a single chain having hooks from which the articles may be suspended spaced apart, singly or in bulk containers or bundles, as appropriate. Preferably, the articles travel in a common equatorial plane of the ECR-X sources. Where necessary, the ECR-X sources may be arranged with equatorial planes that are offset horizontally, angularly, vertically or some combination thereof, to provide an adequate cumulative dose to the articles being treated.

Advantageously, the microwave magnetron sources may be driven by the same motor that operates the conveyor track. For example, a 100 kw gasoline-powered motor typical for operating a conveyor track can be used to produce 25 kw to operate the two magnetrons of this embodiment and to drive the chain conveyor. Such a facility can be constructed in any location where gasoline (or similar fuel source) can be obtained.

If the conveyor path has a length of 25 meters and is advanced at a speed of 1 cm/sec, then the X-ray dose provided is on the order of 2.5 kgy and the yield is on the order of 1 kgy per ten seconds. The faster the conveyor speed the lower the cumulative dose. Thus, the operating parameters can be selected to provide the following yields for the identified products: pork 5 kg per 10 seconds; fresh fruit 2.5 kg per 10 seconds; white potatoes 25 kg per 10 seconds; and poultry 1 kg per 10 seconds.

Advantageously, the entire station, composed of one or several blocks of 24 sources, can be installed on the bed of a large truck or trailer with a 100 kW motor and driven from location to location, for example, for processing grains, fruits and vegetables during harvesting in any location and environment. Either the truck bed may be sealed against X-ray leakage, or the bed may be parked inside a structure that can be sealed to trap X-rays.

It should be understood that the ECR-X source and methods of the present invention also could be used to irradiate articles, products and materials in a batch mode, wherein the X-rays are generated within a X-ray shielded structure and the structure has a platform for supporting the articles to be irradiated and a door (or similar opening) for inserting and removing articles such that the door has appropriate seals against X-ray leakage and interlocks for preventing X-ray generation when the door is open. Door seals could include, e.g., braided wire contact seals, X-ray absorbing dielectric seals, and/or waveguide chokes. The interlock system used may be a dual interlock of the type used in conventional domestic microwave ovens.

Another aspect of the invention is directed to a source and a method for irradiating body tissue with X-rays at a dosage level and for a time sufficient to medical or dental diagnostic or therapeutic purposes. Such methods include generating an ECR plasma to produce X-rays in a given direction, for example, to expose a film for X-ray evaluation of tissue, bone and other structures, including mammography and computer aided tomography (CAT scans). Such methods also include generating an ECR plasma to produce X-rays for medical therapeutics, for example, cancer therapy, diathermy, and activating X-ray responsive drugs. In this regard, the X-ray dosages to be used are those generally used in medical and dental diagnostic and therapeutic practices. Advantageously, the small and light weight of the ECR-X source, together with a lead shield that covers all of the cavity except a suitably shaped window, provide easy maneuverability to locate the source proximate to the patient and easy portability of the apparatus, for example, for a mobile medical clinic. In addition, the small size and simplicity of operation permits providing emergency service vehicles such as ambulances, fire rescue vehicles and the like with portable X-ray machines, which may be hand held, for obtaining X-ray images of injured patients prior to moving them.

One skilled in the art will appreciate that the present invention can be practiced by other than the described embodiments which are presented for purposes of illustration and not of limitation.

I claim:

1. An X-ray source comprising
a microwave source which produces microwaves,
a static magnetic field source which produces a static magnetic field,
a chamber having an inside surface,
a gas inside the chamber, the gas comprising a dense layer of gas atoms lining the inside surface of the chamber, and an electron cyclotron resonance plasma formed from said gas in response to the microwaves and the static magnetic field, the plasma being disposed adjacent the inside surface of the chamber to interact with the dense layer of gas atoms lining the inside surface of the chamber, thereby to produce X-rays.

2. An X-ray source as in claim 1, wherein the chamber is sealed and the pressure within the chamber is $10^{-5}$ to $10^{-4}$ Torr.

3. An X-ray source as in claim 2, wherein the pressure within the chamber is 3 to $8 \times 10^{-5}$ Torr.

4. An X-ray source as in claims 1 or 2, wherein the chamber is spherical in shape.

5. An X-ray source as in claims 1 or 2, wherein the chamber is made of quartz.

6. An X-ray source as in claims 1 or 2, wherein the electron cyclotron resonance plasma contains a closed ring adjacent the inner surface of the chamber.

7. An X-ray source as in claims 1 or 2, wherein the gas inside the chamber is a heavy atomic weight gas.

8. An X-ray source as in claims 1 or 2, wherein the chamber volume is on the order of 100 cm$^3$.

9. The X-ray source of claim 1 wherein the plasma further comprises a hot electron ring within the chamber, wherein the interaction of the hot electron ring within the chamber, wherein the interaction of the hot electron ring and the dense layer of gas atoms lining the inside surface of the chamber produces X-rays.

10. The X-ray source of claim 1 further comprising a microwave resonant cavity for receiving the chamber.

11. An X-ray source comprising
a static magnetic field source which produces a static magnetic field,
a non-vacuumated microwave resonant cavity and a microwave source which produces microwaves in the cavity, and
a sealed chamber within the cavity, said sealed chamber having an inside surface, said sealed chamber further containing a gas comprising a dense layer of gas atoms lining the inside surface of the sealed chamber, and an electron cyclotron resonance plasma produced from the gas in response to the microwaves and the static magnetic field, the plasma being disposed to interact with the dense layer of gas atoms thereby to produce X-rays.

12. An X-ray source as in claims 3 or 10, wherein the chamber is spherical in shape.

13. An X-ray source as in claims 3 or 10, wherein the chamber contains a hot electron ring.

14. An X-ray source comprising:
a non-vacuumated microwave resonant cavity;
a sealed chamber within the cavity containing a low pressure gas comprised of a dense layer of gas atoms lining the inside surface of the chamber;
a microwave source which produces microwave energy;
a microwave coupler for supplying microwave energy from the microwave source to said cavity, and
means for applying a magnetic field to said sealed chamber to produce an electron cyclotron resonance plasma within said chamber said plasma being disposed to interact with the dense layer of gas atoms lining the inside surface of the chamber to thereby produce X-rays.

15. An X-ray source as in claim 14 wherein the gas is a heavy atomic weight gas.

16. The X-ray source as in claim 14 wherein the plasma contains a hot electron ring.

17. The X-ray source as in claim 16 wherein the hot electrons bombard the gas and the chamber to produce X-rays.

18. The X-ray source as in claim 14 wherein the chamber is sealed and has a pressure of from $10^{-5}$ to $10^{-4}$ Torr.

19. The X-ray source as in claim 18 wherein the chamber is spherical in shape.

20. The X-ray source as in claim 18 wherein the means for supplying the magnetic field further comprises a pair of magnets disposed on opposite sides of the chamber and cavity.

21. The X-ray source as in claim 20 wherein the pair of magnets are arranged with opposite poles facing one another.

22. The X-ray source as in claim 21 wherein the magnets are made of SmCo$_5$ and have a magnetic induction on the surface on the order of 0.4 Tesla.

23. The X-ray source as in claim 20 wherein the distance between the magnets is adjustable.

24. The X-ray source as in claims 20, 21, 22 or 23 wherein the microwave energy coupled into the cavity provides an electron cyclotron resonance plasma including a hot electron ring inside the chamber.

25. The X-ray source as in claim 14 further comprising means for removably mounting the chamber inside the cavity.

26. The X-ray source as in claim 25 wherein the removably mounting means includes a non conductive, non magnetic cushion shaped for supporting the chamber.

27. The X-ray source as in claim 26 wherein the non conductive non magnetic material is a porous teflon.

28. The X-ray source as in claim 14 wherein the cavity is made of a material that is transparent to X-ray emission and contains microwave energy.

29. The X-ray source as in claim 28 wherein the material is a mesh grid.

30. The X-ray source as in claim 29 further comprising a coating of a second material for containing X-rays over a first portion of the cavity surface for confining the X-ray emission to a second portion of the cavity.

31. The X-ray source as in claim 14 wherein the cavity further comprises a cylindrical wall secured between two opposing flanges.

32. The X-ray source as in claim 31 wherein the cylindrical wall is a material that is transparent to X-rays and contains microwaves.

33. The X-ray source as in claim 32 wherein the cylindrical wall is a conductive mesh grid.

34. The apparatus as in claim 14 further comprising a platform for supporting an article to be radiated with X-rays and a housing made of a material for containing X-rays for enclosing the chamber and the platform.

35. The apparatus as in claim 34 wherein the housing further comprises a door having an open position and a closed position for inserting and removing an article to be exposed to X-rays and an interlock system so that the X-ray source is disabled from producing X-rays when the door is open and not disabled when the door is securely closed.

36. Apparatus for providing X-ray emissions comprising:
   a source of microwave energy;
   a plurality of X-ray sources, each X-ray source comprising:
      a microwave resonant cavity;
      a sealed vacuumated chamber having an inside surface, the chamber filled with a heavy atomic weight gas or gas mixture located inside the cavity said gas or gas mixture comprising a dense layer of atoms of the gas or gas mixture lining the inside surface of the chamber; and means for applying a magnetic field to the sealed chamber for producing an electron cyclotron resonance plasma adjacent the inside surface of the chamber, so that said plasma interacts with the dense layer of atoms of the gas or gas mixture to produce thereby X-rays;
   and a waveguide network for feeding microwaves from the source to the microwave resonant cavity of each X-ray source.

37. The apparatus of claim 36 further comprising a conveyor line for passing articles to be exposed to X-rays emitted by one or more of the plurality of X-ray sources.

38. The apparatus of claim 37 further comprising a cladding for containing X-rays surrounding the conveyor and plurality of X-ray sources, the cladding having an opening for the entry and exit of articles.

39. The apparatus of claim 36 further comprising a passageway for receiving a product to be exposed to X-rays wherein the plurality of X-ray sources are disposed inside the passageway, and means for advancing the product through the passageway.

40. The apparatus of claim 37 further comprising a movable platform for supporting the microwave energy source, the plurality of X-ray sources, the waveguide network, and the conveyor.

41. The apparatus of claim 40 wherein the platform is a truck bed.

42. The apparatus of claim 36 wherein the microwave source is capable of delivering from 200 to 500 watts of power to each X-ray source.

43. Apparatus for irradiating a material with X-ray radiation comprising:
   a plurality of X-ray sources, each X-ray source comprising:
      a microwave resonant cavity;
      a sealed vacuumated chamber having an inside surface, the chamber filled with a heavy atomic weight gas or gas mixture located inside the cavity said gas or gas mixture comprising a dense layer of atoms of the gas or gas mixture lining the inside surface of the chamber; and
      means for applying a magnetic field to the sealed chamber for producing an electron cyclotron resonance plasma adjacent the inside surface of the chamber, so that said plasma interacts with the dense layer of atoms of the gas or gas mixture to produce thereby X-rays;
   and means for advancing the material to be exposed to X-rays emitted by one or more of the plurality of X-ray sources.

44. The apparatus of claim 43 further comprising a cladding for containing X-rays surrounding the advancing means and plurality of X-ray sources, the cladding having an opening for the entry and exit of materials.

45. The apparatus of claim 43 further comprising a source of microwave energy and a waveguide network for feeding microwaves from the source to the resonant cavity of each of the X-ray sources.

46. The apparatus of claim 43 further comprising a plurality of sources of microwave energy and a waveguide network for feeding microwaves from the sources to the resonant cavity of each of the X-ray sources wherein the waveguide network is configured so that each microwave energy source delivers microwaves to more than one X-ray source.

47. The apparatus of claim 46 wherein the number of X-ray sources fed microwave energy is controlled by selecting the microwave sources turned on and the waveguide network.

48. The apparatus of claims 43, 44 or 46 further comprising a movable platform for supporting the plurality of X-ray sources and the advancing means.

49. The apparatus of claim 48 wherein the platform is a truck bed.

50. The apparatus of claims 43, 44, 45, 46 or 47 wherein the advancing means is a conveyor for supporting the material.

51. The apparatus of claims 43, 44, 45, 46 or 47 wherein the material is a flow and the advancing means further comprises a passageway for confining the material flow and means for passing the material flow through the passageway, the plurality of X-ray sources being disposed inside the passageway.

52. The apparatus of claim 45 wherein the source of microwave energy is capable of providing from 200 to 500 watts of power to each X-ray source to be used.

53. The apparatus of claim 46 wherein each microwave source is capable of providing from 200 to 500 watts of power to each X-ray source to which it delivers energy.

54. A method for producing X-rays comprising:
   (a) providing a vacuumated sealed chamber containing a gas at low pressure said gas comprising a dense layer of gas atoms lining the inside surface of the chamber;
   (b) applying microwaves and a static magnetic field to the chamber; and
   (c) producing an electron cyclotron resonance plasma from said gas having hot electrons within said chamber, said hot electrons bombarding the dense layer of gas atoms lining the inside surface of the chamber to produce X-rays.

55. The method of claim 54 further comprising:
   (d) providing a non-vacuumated microwave resonant cavity containing the chamber.

56. The method of claims 54 or 55 wherein the sealed container contains a heavy atomic weight gas or gas mixture.

57. The method of claims 54 or 55 wherein step (d) further comprises producing a hot electron ring adjacent the inside of the chamber.

58. The method of claims 54 or 55 wherein the chamber has a pressure of from $10^{-5}$ to $10^{-4}$ Torr.

59. The method of claim 58 further comprising providing the chamber with a spherical shape.

60. The method of claim 55 wherein step (f) further comprises disposing a pair of magnets on opposite sides of the chamber and cavity.

61. The method of claim 60 wherein the pair of magnets are arranged with opposite poles facing one another.

62. The method of claims 60 or 61 further comprising forming the magnets of SmCo$_5$ with a magnetic induction on the surface on the order of 0.4 Tesla.

63. The method of claim 60 further comprising adjusting the distance between the magnets to adjust the production of X-rays.

64. The method of claim 55 wherein step (d) further comprises removably mounting the chamber inside the cavity.

65. The method of claim 64 wherein step (d) further comprises removably securing the chamber between non conductive, non magnetic cushions shaped for supporting the chamber.

66. The method of claim 55 wherein step (d) further comprises forming the cavity of a material that is transparent to X-ray emission and contains microwave energy.

67. The method of claim 66 wherein step (d) further comprises forming the cavity of a mesh grid.

68. The method of claims 55 or 67 further comprising coating a first portion of the cavity surface with a second material for containing X-rays for confining the X-ray emission to a second portion of the cavity.

69. The method of claim 55 wherein step (d) further comprises forming a cylindrical wall secured between two opposing flanges.

70. The method of claim 69 wherein step (d) further comprises forming the cylindrical wall of a material that is transparent to X-rays and contains microwaves.

71. The method of claim 70 wherein step (d) further comprises forming the cylindrical wall of a conductive mesh grid.

72. The method of claim 55 wherein step (e) further comprises providing from between 200 to 500 watts of microwave power.

73. A method for providing X-ray emissions comprising:
  providing a plurality of X-ray sources, each X-ray source having a sealed vacuumated ECR chamber filled with a heavy atomic weight gas or gas mixture, each ECR chamber having an inside surface; and
  applying microwaves and a static magnetic field to each ECR chamber to form an electron cyclotron resonance plasma from said gas or gas mixture in each ECR chamber and causing said plasma to interact with a dense layer of atoms of said gas or gas mixture lining the inside surface of each ECR chamber to produce X-rays.

74. The method as in claim 73 wherein each X-ray source has a microwave resonant cavity for receiving the chamber.

75. The method of claim 74 further comprising passing a material to be exposed to X-rays through the X-rays emitted by one or more of the plurality of X-ray sources.

76. The method of claim 75 further comprising containing X-rays emitted by the plurality of X-ray sources with a cladding having an opening for passing the materials into and out of the emitted X-rays.

77. The method of claim 76 wherein there is one opening for passing materials into the X-rays and one opening for passing the materials out of the X-rays.

78. The method of claim 75 further comprising providing a passageway for receiving the material to be exposed to X-rays, disposing the plurality of X-ray sources inside the passageway, and advancing the material through the passageway to be radiated by the sources.

79. The method of claim 75 further comprising supporting the microwave energy source, the plurality of X-ray sources, and the waveguide network, on a movable platform.

80. The method of claim 79 wherein the moveable platform is a truck.

81. The method of claim 74 wherein further comprising coupling microwave power of from 200 to 500 watts to each resonant cavity to be used.

82. A method for irradiating a material with X-ray radiation comprising:
  providing a source of microwave energy;
  providing a plurality of X-ray sources, each X-ray source having a non-vacuumated microwave resonant cavity and a sealed vacuumated chamber having an inside surface and filled with a heavy atomic weight gas or gas mixture, said gas or gas mixture comprising a dense layer of gas atoms lining the inside surface of the chamber, the chamber being located inside the cavity;
  applying a magnetic field to the sealed chamber for producing an electron cyclotron resonance plasma within the chamber adjacent the inside surface of the chamber so that the plasma interacts with said dense layer of gas atoms lining the inside surface of the chamber to produce X-rays;
  feedings microwaves from the microwave source to the resonant cavity of each of the X-ray sources to be used; and
  advancing the material along a path to be exposed to X-rays emitted by one or more of the plurality of X-ray sources.

83. The method of claim 82 further comprising cladding the plurality of X-ray sources and the path with a material for containing X-rays, and advancing the material through an opening in the cladding into and out of the emitted X-rays.

84. The method of claim 83 wherein there is a first opening for passing the material into the X-rays and a second opening for passing the material out of the X-rays.

85. The method of claim 82 further comprising providing a plurality of sources of microwave energy and feeding microwaves from each microwave energy source to one or more X-ray sources.

86. The method of claim 85 further comprising controlling the level of X-ray emissions by selectively feeding microwave energy to a selected number of the plurality of X-ray sources.

87. The method of claims 82, 83 or 85 further comprising supporting the plurality of X-ray sources on a movable platform.

88. The method of claims 82, 83, 85 or 86 wherein advancing the material further comprises supporting the material on a conveyor passing the plurality of X-ray sources.

89. The method of claims 82, 83, 85 or 86 wherein the advancing the material further comprises passing the material through a flow passageway, and disposing the plurality of X-ray sources inside the passageway.

* * * * *